United States Patent [19]

Eibl et al.

[11] Patent Number: 4,640,834

[45] Date of Patent: Feb. 3, 1987

[54] METHOD OF INACTIVATING REPRODUCIBLE FILTERABLE PATHOGENS IN BLOOD PRODUCTS AS WELL AS A METHOD OF PRODUCING BLOOD PRODUCTS

[75] Inventors: Johann Eibl; Otto Schwarz; Fritz Elsinger, all of Vienna; Günter Wöber, Oberwaltersdorf; Anton Philapitsch, Ebenfurt; Yendra Linnau, Vienna; Friedrich Dorner, Vienna; Karl Trambauer, Vienna; Wolfgang Frechinger, Vienna, all of Austria

[73] Assignee: Immuno Aktiengesellschaft fur Chemisch-Medizinische Produkte, Austria

[21] Appl. No.: 705,691

[22] Filed: Feb. 26, 1985

[30] Foreign Application Priority Data

Mar. 9, 1984 [AT] Austria .................................. 792/84
Oct. 11, 1984 [AT] Austria ................................. 3237/84

[51] Int. Cl.$^4$ .................... A61K 37/465; A61K 37/48
[52] U.S. Cl. ..................................... 424/94; 424/101; 514/2
[58] Field of Search ....................... 424/101, 94; 514/2

[56] References Cited

U.S. PATENT DOCUMENTS

| | | |
|---|---|---|
| 4,160,025 | 7/1979 | Eibl et al. . |
| 4,379,085 | 4/1983 | Williams et al. . |
| 4,388,232 | 6/1983 | Eibl et al. . |
| 4,395,396 | 7/1983 | Eibl et al. . |
| 4,424,206 | 1/1984 | Ohmura et al. ...................... 424/101 |
| 4,440,679 | 4/1984 | Fernandes et al. .................. 424/101 |
| 4,446,134 | 5/1984 | Naito et al. .......................... 424/101 |
| 4,481,189 | 11/1984 | Prince .................................. 424/101 |

FOREIGN PATENT DOCUMENTS

| | | |
|---|---|---|
| 0015055 | 9/1980 | European Pat. Off. . |
| 0035204 | 9/1981 | European Pat. Off. . |
| 0053338 | 6/1982 | European Pat. Off. . |
| 0052827 | 6/1982 | European Pat. Off. . |
| 0077870 | 5/1983 | European Pat. Off. . |
| 0094611 | 11/1983 | European Pat. Off. . |
| 2916711 | 11/1980 | Fed. Rep. of Germany . |
| 82/03871 | 11/1982 | PCT Int'l Appl. . |
| 83/04371 | 12/1983 | PCT Int'l Appl. . |

OTHER PUBLICATIONS

Webster's Third New Internat. Dictionary, (1964), p. 929.
XII Internat. Congress on Blood Transfusion, Abstracts, "MIR" Publishers, Moscow 1969, pp. 473-475.
Reed, J. L. and H. Muench; Amer. J. Hyg., 27, 493, (1983).
Scholz, E.; Fresenius', Z. anal. Chem., 314, 567-571 (1983).
Vox. Sang. 33, 37-50, (1977).
Weber and Osborn, in "The Reliability of Morecular Weight . . . ", J. Biol. Chem., 244, 4406, (1969).
Merril et al., in "Ultrasensitive Stain for Proteins . . . ", Science, 211, 1437, (1981).
Vox. Sang. 26, 118, (1974).
M. Kleindel, H. Lang, A. Philapitsch, G. Wöber, "Thrombosis and Haemostasis", 50, 244, (1983).
D. G. Deutsch and E. T. Mertz, in Science, 170, 1095, (1970).
K. C. Robbins, L. Summaria, Methods in Enzymology, 19, 184-186, (1970).
U. S. Pharmacopeia, 16th Revision, (USP XVI, 1960), p. 298.
Journal of Amer. Chem. Cov., 71, 541-550, (1949).

Primary Examiner—Sam Rosen
Attorney, Agent, or Firm—Burns, Doane, Swecker & Mathis

[57] ABSTRACT

A method of inactivating viruses in blood products is described, wherein the blood products are heat-treated in a humid or in a solid state in the presence of inorganic or organic hydroxyl group-containing compounds having an $H^+$-dissociation constant of $<10^{-11}$ in a concentration of more than 0.05 (5% by weight) and less than 0.70 (70% by weight). The hydroxyl group-containing compounds may be water, methanol, ethanol or mannitol. The temperature may amount up to 121° C., the heat treatment may last from 1 s to 100 h. The inactivation method may be applied for producing blood products selected from enzymes, proenzymes including coagulation factors, enzyme inhibitors, immunoglobulins, albumin, plasminogen, fibrinogen, fibronectin or plasma, the inactivation destroying any reproducible filterable pathogens that might be present.

20 Claims, 4 Drawing Figures

Figure 1:
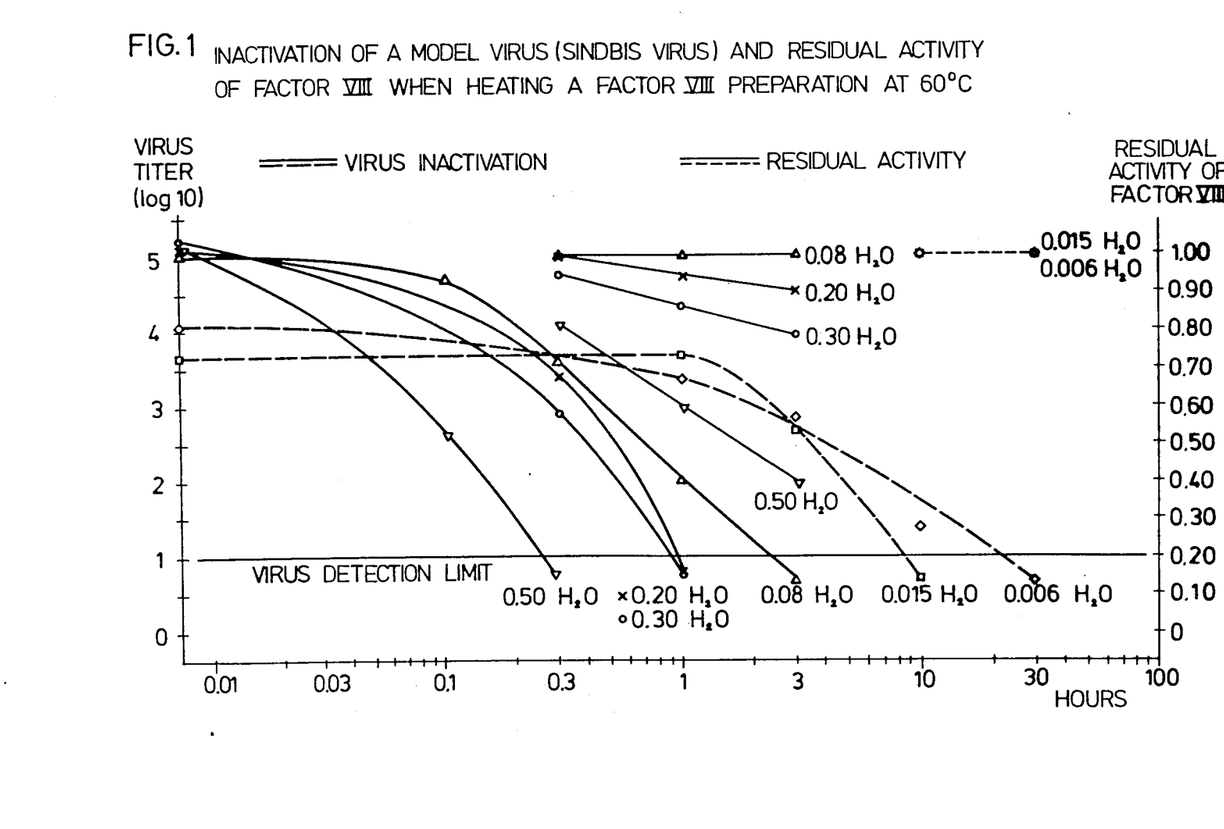

FIG. 1 INACTIVATION OF A MODEL VIRUS (SINDBIS VIRUS) AND RESIDUAL ACTIVITY OF FACTOR VIII WHEN HEATING A FACTOR VIII PREPARATION AT 60°C

Figure 2:
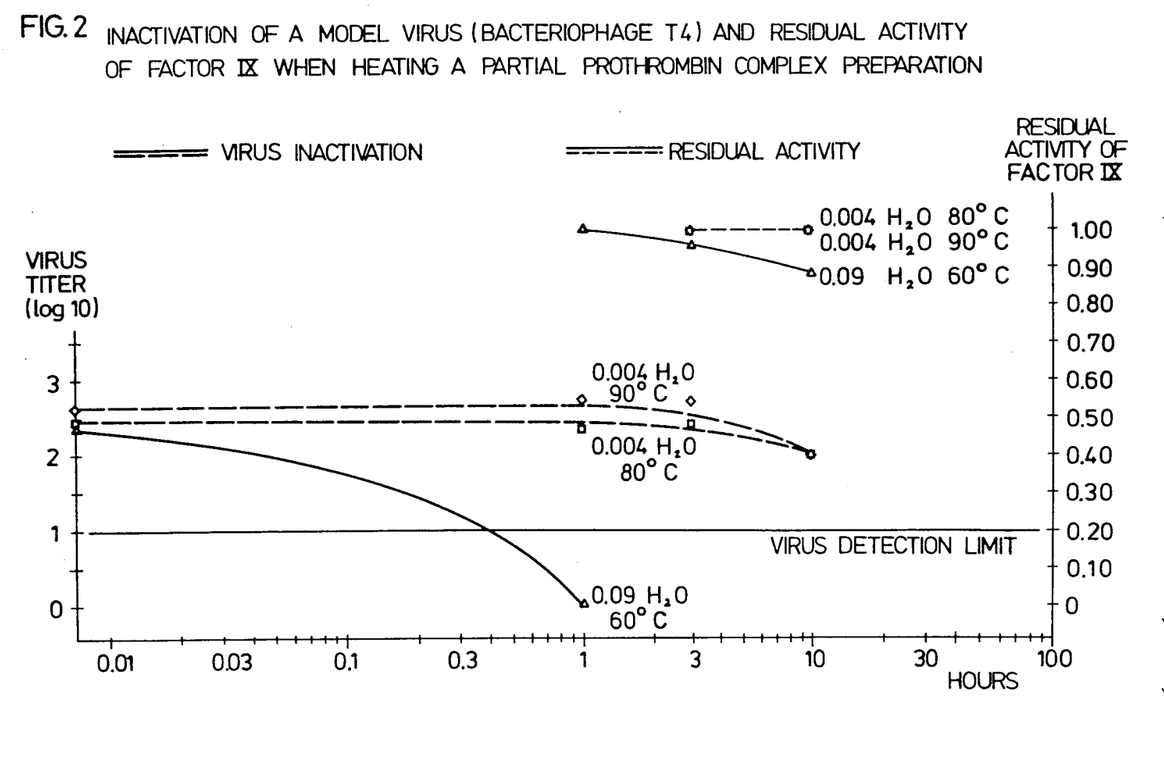

FIG. 2 INACTIVATION OF A MODEL VIRUS (BACTERIOPHAGE T4) AND RESIDUAL ACTIVITY OF FACTOR IX WHEN HEATING A PARTIAL PROTHROMBIN COMPLEX PREPARATION

Figure 3:
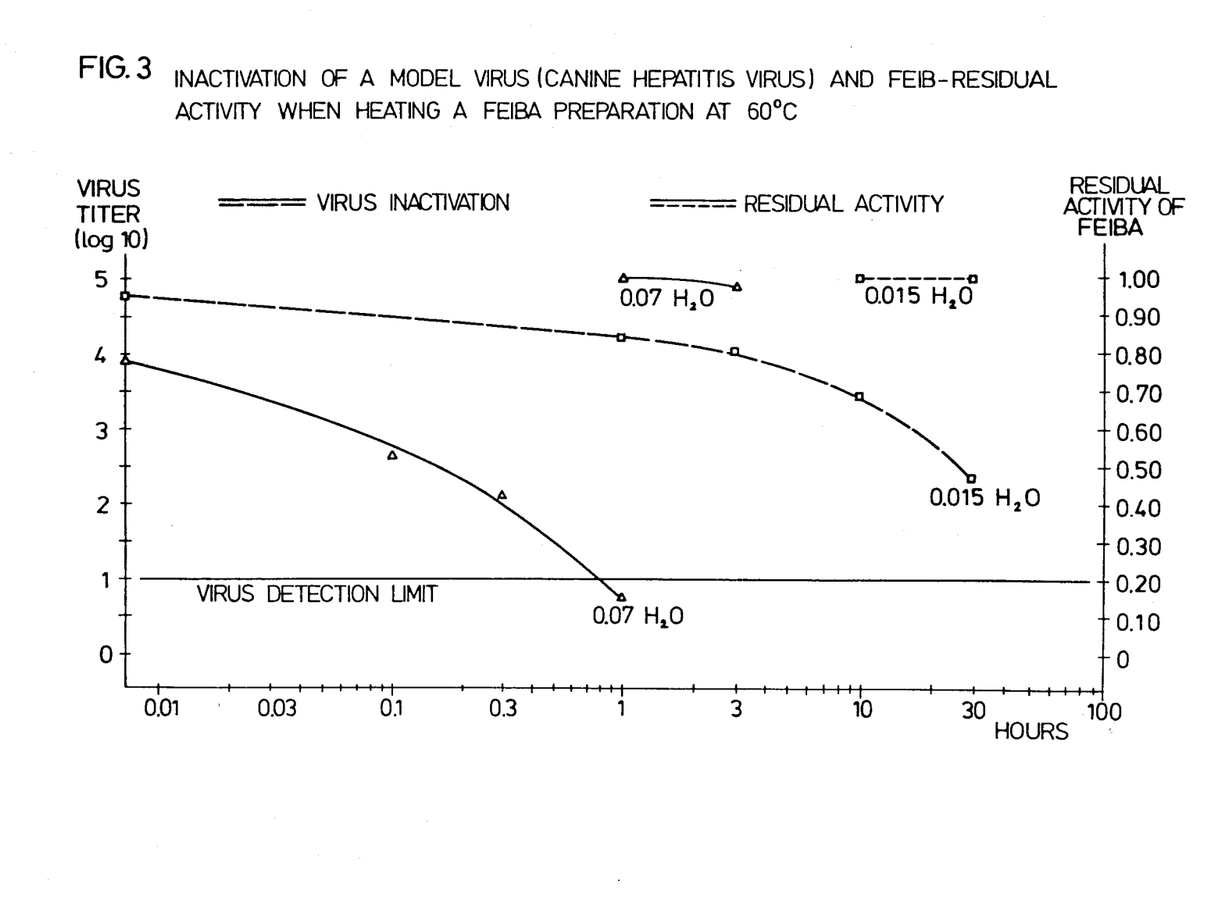

FIG. 3 INACTIVATION OF A MODEL VIRUS (CANINE HEPATITIS VIRUS) AND FEIB-RESIDUAL ACTIVITY WHEN HEATING A FEIBA PREPARATION AT 60°C

METHOD OF INACTIVATING REPRODUCIBLE FILTERABLE PATHOGENS IN BLOOD PRODUCTS AS WELL AS A METHOD OF PRODUCING BLOOD PRODUCTS

The invention relates to a method of inactivating reproducible filterable pathogens, in particular hepatitis viruses and pathogens which may be able to transmit AIDS (acquired immune deficiency syndrome), in blood products by using an elevated temperature, as well as to a method of producing blood products by using this method.

By blood products, products of human or animal blood or plasma are meant which are intended for a therapeutic, prophylactic or diagnostic use. Such products may contain enzymes, proenzymes including coagulation factors, enzyme inhibitors, immunoglobulins, albumin, plasminogen, fibrinogen, fibronectin or plasma.

There are abundant publications dealing with the thermal inactivation of reproducible filterable pathogens in blood products.

The various methods include:
heating of the blood products in aqueous solution, if desired, with the addition of virucidal substances,
heating of the blood products in aqueous solution in the presence of stabilizing agents,
treating the blood products with organic solvents,
irradiating the blood products in the solid state,
heating of the blood products in the dry state.

All these inactivation methods aim at destroying the potential infectivity of the preparations while substantially maintaining their biological activity. Up to now, however, this aim could be achieved only with albumin preparations, i.e. by heating aqueous albumin solutions at a temperature of 60° C. for 10 hours, since albumin is considerably more stable towards heat than all other blood proteins.

In detail, the following publications should, for instance, be listed with regard to the prior art.

German Offenlegungsschrift No. 29 16 711 discloses a method of treating coagulation factor-containing preparations in aqueous solution by applying a temperature of from 30° C. to 100° C., wherein an amino acid and a monosaccharide, an oligosaccharide or a sugar alcohol are added to the solution of the coagulation factors.

Published European Patent Application EP A2-0 053 338 discloses a method of inactivating hepatitis viruses in preparations containing Factors IX and X, wherein the aqueous solution of a blood preparation is heated in the presence of calcium ions and, if desired, an amino acid and/or a saccharide or sugar alcohol, at temperatures of up to 100° C.

Published European Patent Application EP A2-0 035 204 discloses a method of inactivating aqueous protein solutions which may contain Factor VIII, fibronectin, globulin, fibrinogen and other proteins, wherein the composition is mixed with a polyol and the mixture is heated at a temperature of from 60° C. to 75° C.

Published European Patent Application EP A2-0 052 827 discloses a method of inactivating hepatitis viruses in an aqueous solution containing the factors II and VII in the presence of a chelating agent and, if desired, an amino acid and/or a saccharide or sugar alcohol.

U.S. Pat. No. 4,379,085 discloses a method of thermally inactivating a plasma protein, such as $C_1$ inhibitor or Factor IX, in an aqueous solution in the presence of potassium or ammonium citrate.

Published European Patent Application EP A2-0 077 870 discloses an inactivation method, wherein an aqueous solution containing Factor VIII is heated at a temperature of from 50° C. to 80° C. together with amino acids, monosaccharides, oligosaccharides, sugar alcohols and hydrocarbon-carboxylic acids or hydroxyhydrocarboncarboxylic acids having 3 to 10 carbon atoms.

PCT application No. WO 83/04371 discloses a method of inactivating hepatitis viruses, wherein a preparation containing the virus is treated at a temperature of from 4° C. to 40° C. with a halohydrocarbon, in particular chloroform.

European Patent B1-0 015 055 discloses a method of treating a blood product, wherein the product, freed of water, is subjected to microwave irradiation in order to inactivate any microorganisms present.

In a treatise of the XII International Congress on Blood Transfusion, Abstracts, "MIR" Publishers, Moscow 1969, pp. 473–475, Rosenberg et al. disclose a method of inactivating albumin-containing preparations and fibrinogen in the dry state by heating at 60° C. for 10 hours.

Published European Patent Application EP A2-0 094 611 discloses a method of treating a Factor VIII-containing composition in the dry state with less than 5% by weight (0.05) water by using a temperature of at least 60° C. for inactivating hepatitis viruses present.

Published PCT-application WO 82/03871 discloses a method of treating preparations containing blood coagulation enzymes, wherein the former are heated in the dry state for inactivating any infectious viruses present; as the dry state, a state with less than 5% by weight (0.05) water is defined.

As can be seen from the above survey, both, methods in which the blood protein-containing preparation to be treated is present in an aqueous solution or suspended in an organic solvent, as well as method in which the preparations are subjected to the inactivation treatment in the dry state, e.g. lyophilized, are known. Despite all the efforts hitherto made, it has not been possible so far to develop an inactivation method which—comparable to the inactivation of the blood product albumin—equally ensures that no hepatitis viruses and other pathogenic viruses can be transmitted and that the biological activity of the respective blood product is maintained. For 30 years, albumin-containing solutions that had been heated to 60° C. for 10 hours in the presence of suitable stabilizing agents have been clinically applied in millions of cases, without infectious diseases having been transmitted thereby. As could be illustrated in experiments with chimpanzees, hepatitis viruses that had been added to albumin-containing solutions are completely inactivated by heating these solutions at 60° C. for 10 hours.

The invention has as its object to provide an inactivation method with which the biological activity of the blood product is maintained and which simultaneously gives the blood product a reliable safety with regard to viruses, in particular hepatitis viruses, equal to or even excelling that obtained in the inactivation of albumin-containing solutions.

According to the invention, this object is achieved with a method of the initially defined kind by heat-treating the blood products in a humid or solid state in the presence of inorganic or organic hydroxyl group-containing compounds having an $H^+$-dissociation constant of $<10^{-11}$ at a temperature in the range of up to 121° C., the concentration of the hydroxyl group-containing compounds being more than 0.05 (5% by weight) and less than 0.70 (70% by weight). The permissible water content is partly dependent on the blood product being treated; in any case, the solid state of the product must be maintained, i.e. a liquid consistency must be avoided.

Since the tests necessary to determine effective inactivation of hepatitis viruses in blood products cannot be carried out on man immediately, and chimpanzees are available in insufficient numbers only, according to the present invention the evaluation of the efficacy of the inactivation is carried out with the help of model viruses. Taking the canine hepatitis virus as a model virus as an example, it could be illustrated that the known methods of virus inactivation in blood products initially mentioned are by far inferior to the inactivation method in albumin. Thus, e.g., canine hepatitis virus in protein solutions in the presence of 0.50 sucrose and 2M glycin as stabilizers is not inactivated; and neither is it in Factor VIII-preparations in the dry state by heating at 60° C. for 10 h. Yet canine hepatitis viruses are completely inactivated in albumin solutions, when heated at 60° C. for 10 h. The same holds true for *E. coli* bacteriophage T4.

Evaluation of the method according to the invention has shown canine hepatitis virus and other model viruses to be completely inactivated. The inactivation rate of *E. coli* bacteriophage T4 in any desired blood product in the presence of the amount of hydroxyl group-containing compounds that is effective according to the invention is even greater than in an albumin solution heated at 60° C.

The duration of the heat treatment according to the invention may be varied within wide limits, depending on the temperature applied and on the type or heat sensitivity of the blood products to be treated. It may be between 1 s and 100 h.

As the hydroxyl group-containing compounds having an H+-dissociation constant of $<10^{-11}$ that may be applied according to the invention, in particular water, methanol, ethanol or mannitol may be used, the concentration of these compounds preferably being of from 0.05 to 0.40. The H+-dissociation constant of water is $10^{-14}$, that of methanol is $10^{-15}$, that of ethanol is $10^{-15}$ and that of mannitol is less than $10^{-17}$.

If water is used, a preferred embodiment of the invention comprises carrying out the heat treatment on preparations containing of from 0.06 to 0.30 water, at a temperature of from 50° C. to 90° C. Furthermore, it has proven very favorable to carry out the heat treatment of the blood products in the presence of an inert protective gas free of oxygen, preferably nitrogen, and if desired in the presence of oxygen-binding substances. With the embodiment in which protective gas is used, it has proven that the residual activities or yields of the blood products, in particular of the coagulation factors, are substantially higher than when heating in an oxygen-containing atmosphere, while the virus inactivation is equally high with regard to its extent and rate.

A further preferred embodiment of the method according to the invention may also consist in that the blood products are heat-treated in a liquid medium in which they are insoluble. As the liquid medium, chloroform or acetic acid ethyl ester may be used.

According to a modified embodiment, the blood products are treated with hydroxyl group-containing gaseous compounds, provided that the concentration of the hydroxyl group-containing compounds of more than 0.05 (5% by weight) and less than 0.70 (70% by weight), preferably less than 0.40 (40% per weight) is achieved in the blood products. With this embodiment, the blood products may, e.g., be treated in the solid state with water vapor having a pressure or partial pressure of between 0.1 and 2 bar.

The inactivation method according to the invention may be used with advantage with a method of producing blood products selected from enzymes, proenzymes including coagulation factors, enzyme inhibitors, immunoglobulins, albumin, plasminogen, fibrinogen, fibronectin or plasma or mixtures of individual blood products, the inactivation being carried out at any desired stage of the production method, whereupon, if desired, the blood products are converted into a galenic or pharmaceutical preparation.

The procedure of using a blood product that is covalently bound to a water-insoluble matrix is also within the scope of the present invention. Thus, e.g., immunoglobulin may be immobilized on sepharose and subjected to an inactivation. On the other hand, it is also possible that a blood product is non-covalently bound to a tissue-compatible carrier, such as a collagen fleece, and is heat-treated. With the production of a fibrinogen-containing preparation, a particular embodiment consists in that a fibrinogen-containing composition is applied onto a tissue-compatible carrier, such as a collagen fleece, and heat-activated.

Within the framework of the production method according to the invention also further fractionation steps may be applied in order to remove neoproteins or neoantigens which might have been formed during the heat inactivation from heat-inactivated blood products.

The inactivation method according to the invention as well as the production of blood products using this method, the effects obtained and the superiority compared with known methods are explained in more detail in the following examples and tables.

EXAMPLE 1

(a) Production of a Factor VIII-preparation.

6,660 ml of fresh frozen plasma was thawed at a temperature of from 0° C. to +4° C. The cryoprecipitate formed was separated by centrifugation and dissolved in 700 ml of trisodium citrate solution containing 0.05 mg of sodium ptenosane sulfate per ml and 30 units of aprotinin per ml. The pH and the temperature of the solution were adjusted to 6.3 and +4° C., respectively. The precipitate formed was separated by centrifugation and discarded.

By adding ethanol up to a concentration of 0.08 the Factor VIII-containing fraction was precipitated. The precipitate formed was separated by centrifugation and dissolved in a glycin-citrate-NaCl-buffer.

(b) Inactivation of a model virus.

The Factor VIII-containing solution obtained in the manner described was adjusted to 50 mg of protein/ml, admixed with a Sindbis virus suspension in cell culture medium TCM 199 or with TCM 199 free of virus, respectively, and freeze-dried. The freeze-dried Factor VIII concentrate was adjusted to various water contents, i.e. to 0.08, 0.20, 0.30 and 0.50, and heated in closed containers at a temperature of either 60° C. or 80° C. for various periods of time. Three samples each were taken prior to heating and at certain times during the heating process for measuring the virus titer, on the one hand, and the residual activity and the water content, on the other hand.

The virus titer was determined in the following manner:

The Factor VIII-containing lyophilisate was dissolved in water and serially diluted with isotonic saline solution in the ratio 1:10. The titer of the Sindbis virus was determined by evaluating the cytopathic effect on sensitive Vero cells in a microtiter plate. After a statistical evaluation, the results were expressed according to the formula of Reed and Muench as logarithm $TCID_{50}$ (Reed J. L. and H. Muench; Amer. J. Hyg. 27, 493, (1938)).

(c) Determination of the residual activity on samples free of virus.

The determination of the residual activity of Factor VIII was effected by using the thromboplastin-generation test (2-stages assay). The residual activity of Factor VIII was calculated by forming the quotient of the Factor VIII activity of the heated sample and the Factor VIII activity of the corresponding non-heated sample.

(d) Determination of the water content on samples free of virus.

The freeze-dried Factor VIII concentrate was extracted with anhydrous methanol before and after the heat treatment. The water content of the methanol solution was determined according to Karl Fischer in a titrator according to the coulometric method (Scholz, E.; Fresenius' Z. anal. Chem. 314, 567–571 (1983)).

The virus titer measured after heat treatment and the residual activity still present after the treatment can be taken from Table 1, which clearly shows that the inactivation rate is dependent on the water content. When using a temperature of 60° C., the virus detection limit is reached with a water content of 0.08 after 3 h, with a water content of 0.20 and 0.30 already after one hour, and with a water content of 0.50 already after 0.3 h. The inactivation effect is also dependent on the temperature. With a temperature of 80° C. and a water content of 0.08, the virus detection limit is reached already after 0.3 h.

With all samples having a water content of up to 0.30 the residual activity after the inactivation treatment was satisfactory with at least 0.80 (80%), and even with a water content of 0.50, the residual activity after 3 h at 60° C. was still 0.38 (38%).

In comparison, Factor VIII concentrates produced in the same manner as described above were treated in the "dry state", i.e. with a water content of less than 0.05 water which corresponds to the "dry state" according to the prior art. The results are listed in Table Ia, from which it becomes apparent that with the low water content that corresponds to the "dry state", the virus detection limit is reached after 10 h only with a water content of 0.015, and after 30 h only with a water content of 0.006. From this there follows that the method according to the present invention is 10 to 100 times more effective in the reduction of a virus titer by 3 to 4 powers of ten.

This superiority of the method according to the present invention as compared to the prior art also is illustrated very clearly by the virus inactivation curves in FIG. 1 of the drawings, in which the curves in full lines illustrate the inactivation according to the invention at 0.50, 0.30, 0.20 and 0.08 $H_2O$, and the curves in broken lines illustrate the virus titer decline in the "dry state" of 0.015 $H_2O$ and 0.006 $H_2O$. On the abscissa in FIG. 1, the duration of the treatment in hours is plotted in logarithmic scale and on the ordinate, the virus titer is plotted in logarithmic scale. In FIG. 1, the course of the residual activity is additionally indicated, the full curves representing the water content according to the invention and the broken curves representing the course of the residual activity in the dry state.

EXAMPLE 2

A Factor VIII-containing solution produced in the same manner as in Example 1 was mixed with a Sindbis-virus suspension in cell culture medium TCM 199 or with TCM 199 free of virus and freeze-dried. The freeze-dried Factor VIII concentrate was subjected to the inactivation treatment in the presence of methanol at a temperature of 60° C. A further Factor VIII-containing solution was mixed with mannitol, freeze-dried and also heat-inactivated at 60° C.

The virus titers measured after the heat-treatment can be seen in Tables II and III, Tables IIa and IIIa giving the comparative results without the content of hydroxyl group-containing compounds according to the invention. Again, the superiority of the procedure of the invention is apparent, in that with the latter the inactivation rate of the model virus is substantially greater while the residual activity is maintained.

EXAMPLE 3

(a) Production of a preparation containing the partial prothrombin complex:

A preparation containing the coagulation Factors II, IX and X was obtained from human plasma according to the method described in Vox. Sang. 33, 37–50 (1977) by adsorption on DEAE-Sephadex, washing of the ion exchanger and elution of the complex.

(b) Inactivation of a model virus.

The eluate was dialyzed, freeze-dried, and an aqueous solution of the partial prothrombin complex having a content of 50 mg of protein/ml was prepared therefrom. The solution was admixed to a suspension of the bacteriophage T4 in culture medium of Escherichia coli 11303 or with culture medium free from virus and freeze-dried. The freeze-dried concentrate was adjusted to a water content of 0.09. Closed containers with freeze-dried partial prothrombin complex samples—with and without virus—were heated at a temperature of 60° C. for various periods of time. Three samples each were drawn prior to heating and at certain times during the heating process for measuring the virus titer on the one hand, and the residual activity and the water content, on the other hand.

The virus titer was determined in the following manner:

The lyophilisate containing the partial prothrombin complex was dissolved in water after the heat treatment and serially diluted with 1 mM $MgCl_2$ at the ratio of 1:10. A mixture of 3 ml of 0.7% Bacto-agar, 43° C. to 45° C., 100 μl suspension of E. coli in liquid medium and 200 μl of the bacteriophage-containing sample or dilution was mixed and rapidly poured onto a nutrient agar plate (ATCC 129). After incubation overnight at 37° C., the plaques produced by reproducible virus particles in the confluent cell layer were counted with the help of a counting apparatus (PFU, plaque-forming units). The results were expressed as $\log_{10}$ PFU.

(c) Determination of the residual activity on samples free of virus.

The Factor IX activity was determined by adding the sample to be tested to a Factor IX-deficient plasma and determination of the activated partial thromboplastin time (1-stage assay). The residual activity of Factor IX of a heated sample was calculated by forming the quotient of the Factor IX activity of the heated sample and the Factor IX activity of the corresponding non-heated sample.

(d) Determination of the water content on samples free of virus.

This determination was effected in the same manner as described in Example 1.

The virus titers measured after the heat treatment and the residual activity still present after the treatment can be seen from Table IV, which shows that the virus detection limit was reached already after a short time—less than 1 h—the residual activity being fully maintained. In comparison thereto, Table IVa shows that when heat-treating partial prothrombin complex preparations in the "dry state" with a water content of 0.004, even after a ten-hour-treatment the virus titer was comparatively high with 2.0, even when higher temperatures of 80° C. and 90° C. were used.

The virus inactivation curves and the course of the residual activities according to this example are illustrated in FIG. 2 in the same manner as in FIG. 1 by full lines, while the curves obtained according to the prior art in the dry state are indicated in broken lines.

EXAMPLE 4

(a) Production of a preparation containing the total prothrombin complex.

A preparation containing the coagulation Factor VII was produced from human citrated plasma according to the method disclosed in U.S. Pat. No. 4,388,232. After separation of the cryoprecipitate and a DEAE-Sephadex treatment, Factor VII was adsorbed on Al(OH)$_3$. Al(OH)$_3$ was subjected to a washing procedure and a Factor VII elution procedure at an increased ionic strength. The Factor VII-containing eluate was dialysed and admixed with the dialysed partial prothrombin complex preparation produced according to Example 3 in such a ratio that the coagulation activities of the Factors II, IX, X and VII were approximately equally high.

(b) Inactivation of a model virus.

The solution of the total prothrombin complexes obtained in the manner described, was adjusted to 50 mg of protein/ml and mixed with Sindbis virus suspension in cell culture medium TCM 199 or with TCM 199 free of virus and freeze-dried. The freeze-dried concentrate was adjusted to a water content of 0.07. Closed containers with the freeze-dried total prothrombin complex samples—with and without virus—were heated at a temperature of 60° C. for various periods of time. Three samples each were drawn prior to heating and at certain times during the heating process for measuring the virus titer, on the one hand, and the residual activity and the water content, on the other hand. The determination of the virus titer was effected in the same manner as described in Example 1.

(c) Determination of the residual activity on samples free of virus.

The determination of the Factor IX activity was effected by adding the sample to be tested to a Factor IX deficient plasma and determining the activated partial thromboplastin time (1-stage assay). The Factor IX-residual activity of a heated sample was calculated by forming the quotient of the Factor IX activity of the sample heated and the Factor IX activity of the corresponding non-heated sample.

(d) Determination of the water content on samples free of virus.

This determination was effected in the same manner as described in Example 1.

The virus titer measured after the heat treatment and the residual activity still present after the treatment can be taken from Table V, which shows that the virus detection limit had been reached after a treatment time of 3 h, the residual activity being substantially maintained.

EXAMPLE 5

(a) Production of a FEIBA preparation.

A FEIBA-containing preparation was produced from fresh frozen human citrated plasma according to the method described in U.S. Pat. No. 4,395,396, in that after thawing of the plasma, separation of the cryoprecipitate forming thereby, and generation of the FEIBA-activity, the coagulation factors were obtained by adsorption on an ion exchanger and elution.

(b) Inactivation of a model virus.

The FEIBA-containing solution obtained was adjusted to 50 mg of protein/ml and mixed with a Sindbis virus suspension in cell culture medium TCM 199 or with TCM 199 free of virus and freeze-dried. The freeze-dried FEIBA concentrate was adjusted to various water contents, i.e. to 0.07, 0.08 and to an ethanol content of 0.10 and heated for various periods of time in closed containers at either 60° C. or 90° C. Three samples each were drawn prior to heating and at certain times during the heating process for measuring the virus titer, on the one hand, and for determining the residual activity and the water content, on the other hand.

The determination of the virus titer was effected in the same manner as described in Example 1.

(c) Determination of the residual activity on samples free of virus

The determination of residual FEIB-activity was effected as described in U.S. Pat. No. 4,160,025, by adding the sample to be tested to a Factor VIII inhibitor plasma and determining the activated partial thromboplastin time (1-stage assay). The residual FEIB-activity of a heated sample was calculated by forming the quotient of the FEIB-activity of the heated sample and the FEIB-activity of the corresponding non-heated sample.

(d) Determination of the water content on samples free of virus.

This determination was effected in the same manner as described in Example 1.

The virus titer measured after the heat treatment and the residual activity still present after the treatment can be taken from Table VI, which shows that the inactivation rate is dependent on the water content as well as on the inactivation temperature. With a water content of 0.07 and a temperature of 60° C., the virus detection limit is reached after 3 h, and with a water content of 0.08 and a temperature of 90° C., the virus detection limit is reached already after 0.2 h. The residual activity is satisfactory in all the cases.

In comparison thereto, a comparative example is listed in Table VIa, a FEIBA sample having been treated in the "dry state" with a water content of 0.009 at 60° C. With 1.7 the virus titer is comparatively high even after 30 h of treatment.

The inactivation of a FEIBA preparation produced according to this example was additionally tested on a second model virus, namely certain hepatitis virus, the freeze-dried FEIBA concentrate having been adjusted to a water content of 0.07 and the treatment temperature being 60° C. and 80° C., respectively. The virus titers measured after the heat treatment can be taken from Table VII. The titer of the canine hepatitis virus was determined by evaluating the cytopathic effect on sensitive MDCK cells in the microtiter plate. After a statistical evaluation, the results were expressed according to the formula of Reed and Muench as logarithm $TCID_{50}$ (Reed J. L. and H. Muench; Amer. J. Hyg. 27, 493 (1938)). From the determination of the virus titer there followed that with a water content of 0.07 and a temperature of 60° C., the virus detection limit was reached after 1 h, with a temperature of 80° C. even after 0.1 h.

Table VIIa again gives a comparative example, the treatment having been effected in the "dry state" with the result that even after 30 h of treatment, the inactivation was still insufficient.

In FIG. 3 the virus inactivation curves and the residual activities according to this Example are illustrated in the same manner as in FIG. 1.

EXAMPLE 6

(a) Production of an immunoglobulin-containing preparation.

An immunoglobulin-containing preparation was obtained from human plasma according to the alcohol fractionation method described by Oncley et al. In the Journal of Amer. Chem. Soc., 71, 541–550 (1949). The solution contained 100 mg of protein, 14 mg of glycin and 1.9 mg of NaCl per ml.

(b) Inactivation of a model virus.

The aqueous solution obtained was mixed with a Sindbis virus suspension in cell culture medium TCM 199 or with TCM 199 free of virus and freeze-dried. The freeze-dried immunoglobulin concentrate was adjusted to a water content of 0.054 and heated for various periods of time in closed containers—with and without virus—at a temperature of 60° C. Three samples each were drawn prior to heating and at certain times during the heating procedure for measuring the virus titer, on the one hand, and for determining the molecular integrity and the water content, on the other hand.

The determination of the virus titer was effected in the same manner as described in Example 1.

(c) Determination of the molecular integrity on samples free of virus.

The determination was effected by comparing the protein compositions of the heated and the non-heated sample, the protein mixtures being separated in the electrical field by means of ($c_1$) cellulose acetate electrophoresis and ($c_2$) SDS-polyacrylamide gel electrophoresis (SDS-PAGE).

($c_1$) Micro-zone electrophoresis on cellulose acetate membrane (Beckman-system).

The electrophoresis was effected according to the Beckman system (Microzone Electrophoresis Manual, Beckman Instructions 015-083630-C, 1977), wherein the samples were applied onto a cellulose acetate membrane equilibrated with veronal buffer (pH 8.6), and subsequently the proteins were separated at 250 V (current 3–4 mA per membrane, run time 20 min). After fixation, there followed staining with Ponceau S, drying, and densitometric evaluation of the membrane.

($c_2$) SDS-polyacrylamide gel electrophoresis (SDS-PAGE).

The electrophoretic separation of the proteins loaded with sodium dodecyl sulfate (SDS) was effected in a 5% polyacrylamide gel according to the method described by Weber and Osborn in "The Reliability of Molecular Weight Determinations by Dodecyl Sulfate-Polyacrylamide Gel Electrophoresis", J. Biol. Chem. 244, 4406 (1969). Staining of the separated proteins was effected according to the method described by Merril et al. in "Ultrasensitive Stain for Proteins in Polyacrylamide Gels Shows Regional Variation in Cerebrospinal Fluid Proteins", Science 211, 1437 (1981), with the help of the silverstaining reagent set of BIO-RAD (Bulletin 1089).

(d) Determination of the water content on samples free of virus.

This determination was effected in the same manner as described in Example 1.

The virus titers measured after the heat treatment and the result of the molecular integrity determination can be taken from Table VIII.

EXAMPLE 7

(a) Production of a $C_1$-esterase inhibitor preparation.

A $C_1$-esterase inhibitor-containing preparation was obtained from human plasma according to the method described in Vox. Sang, 26, 118 (1974) by adsorption on an anion exchanger (DEAE Sephadex) and subsequent elution. After salt precipitation for separating undesired proteins, the purified $C_1$-esterase inhibitor preparation was freeze-dried.

(b) Inactivation of a model virus.

An aqueous solution obtained from the lyophilisate of the $C_1$-esterase inhibitor preparation was adjusted to 50 mg of protein/ml and mixed with a Sindbis virus suspension in cell culture medium TCM 199 or with TCM 199 free of virus and freeze-dried again. The concentrate was adjusted to a water content of 0.10 and heated in closed containers— with and without virus—at a temperature of 60° C. Three samples each were drawn prior to heating and at certain times during the heating process for measuring the virus titer, on the one hand, and the residual activity and the water content, on the other hand.

The determination of the virus titer was effected in the same manner as described in Example 1.

(c) Determination of the residual activity on samples free of virus.

The activity of the $C_1$-esterase inhibitor was determined via its ability to inhibit the hydrolysis of the chromogenic substrate C1-1 (Pentapharm) by $C_1$-esterase, according to M. Kleindel, H. Lang, A. Philapitsch, G. Wöber, "Thrombosis and Haemostasis", 50, 244 (1983).

(d) Determination of the water content on samples free of virus.

This determination was effected in the manner described in Example 1.

The virus titer measured after the heat treatment and the residual activity still present after the treatment can be taken from Table IX.

EXAMPLE 8

(a) Production of a plasminogen-containing preparation.

A plasminogen-containing preparation was produced according to the method described by D. G. Deutsch 
and E. T. Mertz in Science 170, 1095 (1970). 50 ml of lysin-sepharose were equilibrated in a column with 0.1M phosphate, pH 7.4. 340 ml of plasma were diluted with water to 640 ml, and the column was loaded with this solution. After removal of the accompanying proteins by washing with 0.3M phosphate solution (pH 7.4), plasminogen was eluted with 0.2M 6-aminocaproic acid (pH 7.4). The plasminogen-containing solution was dialysed to remove 6-amino caproic acid and subsequently freeze-dried.

(b) Inactivation of a model virus.

An aqueous solution of the plasminogen produced from the lyophilisate was adjusted to 50 mg of protein/ml and mixed with a Sindbis virus suspension in cell culture medium TCM 199 or with TCM 199 free of virus and freeze-dried again. The concentrate was adjusted to a water content of 0.08 and heated in closed containers—with and without virus—at a temperature of 60° C. Three samples each were drawn prior to heating and at certain times during the heating process for measuring the virus titer, on the one hand, and the residual activity and the water content, on the other hand.

The determination of the virus titer was effected in the same manner as described in Example 1.

(c) Determination of the residual activity on samples free of virus.

This determination was effected such that a plasminogen-containing sample was activated with streptokinase to plasmin according to the method of K. C. Robbins, L. Summaria, Methods in Enzymology, 19, 184–186 (1970), and the liberated plasmin activity was determined by quantitation of the TCA-soluble split products liberated from casein.

The virus titers measured after the heat treatment and the residual activity still present after the treatment can be taken from Table X, which shows that the virus detection limit was reached after 5 h with a satisfactory residual activity.

EXAMPLE 9

(a) Production of a plasma preparation.

Blood from healthy donors were taken in a blood collection bag containing trisodium citrate solution. After the mixture has been gently mixed, it was centrifuged. The supernatant plasma was decanted; 400 ml of plasma were mixed with 22 ml of a 15% glycin solution, pH 3.6.

(b) Inactivation of a model virus.

The plasma buffered with glycin was mixed with a Sindbis virus suspension in cell culture medium TCM 199 or with TCM 199 free of virus, freeze-dried and adjusted to a water content of 0.08. Closed containers with the plasma samples—with and without virus—were heated for various periods of time at 60° C. Three samples each were drawn prior to heating and at certain times during the heating process for measuring the virus titer, on the one hand, and the residual activity and the water content, on the other hand.

The determination of the virus titer was effected in the same manner as described in Example 1.

(c) Determination of the residual activity on samples free of virus.

This determination was effected by assaying the activated partial thromboplastin time (aPTT) of the plasma, in that the coagulation time of a mixture of 0.1 ml each of plasma, kaolin/phospholipid suspension and 0.025 molar calcium chloride was measured. The residual activity of a heated sample was calculated by forming the quotient of the aPTT of the non-heated sample and the aPTT of the corresponding heated sample.

(d) Determination of the water content on samples free of virus.

This determination was effected in the same manner as described in Example 1.

The virus titers measured after the heat treatment and the residual activity still present after the treatment can be taken from Table XI, which shows that the virus detection limit was reached already after 0.3 h with a satisfactory maintenance of the residual activity.

EXAMPLE 10

(a) Production of a fibrinogen and fibronectin-containing preparation.

After separating the cryoprecipitate and the prothrombin complex components from human plasma, the supernatant formed was cooled to 0° C., and ethanol was added under stirring in an amount so as to obtain a final concentration of 0.08 (8%). The temperature was adjusted to −2° C., and the pH value to 7.0. The suspension was centrifuged, and the pasty precipitate obtained, which contained fibrinogen and fibronectin was washed with a citrated glucose—pH 6.9—buffered 6.5% ethanol solution until in the supernatant not more than 0.5 mg of protein/ml could be detected. The purified fibrinogen was frozen and freeze-dried so as to remove ethanol.

(b) Inactivation of a model virus.

An aqueous solution of the lyophilisate was adjusted to 50 mg of protein/ml and admixed with a Sindbis virus suspension in cell culture medium TCM 199 and with TCM 199 free of virus, respectively, and freeze-dried again. The concentrate was adjusted to a water content of 0.08 and heated in closed containers—with and without virus—at a temperature of 60° C. Three samples each were taken prior to heating and at certain times during the heating process for determining the virus titer, on the one hand, and the residual activity and the water content, on the other hand.

The determination of the virus titer was effected in the same manner as described in Example 1.

(c) Determination of the residual activity on samples free of virus.

This determination was effected ($c_1$) with a potency test (thrombin time), wherein the potency of a fibrinogen solution was determined according to the U.S. Pharmacopeia, 16th revision (USP XVI, 1960), page 298, in that a sample of a fibrinogen solution was mixed with calcium chloride and thrombin, and the coagulation time was determined. The residual activity was calculated by forming the quotient of the coagulation time of the non-heated sample and the coagulation time of the heated sample; and ($c_2$) with the determination of the clottable protein.

The clottable protein of a fibrinogen solution was determined according to USP XVI, page 298, in that (1) the total protein content of the fibrinogen solution was determined (nitrogen determination according to Kjeldahl), and (2) the protein content of the fibrin clotted after the addition of thrombin was determined according to the same method (Kjeldahl). The quotient of the protein value of the fibrin (2) and the protein value of the total protein (1) gave the clottable protein.

The residual activity was calculated by forming the quotient of the clottable protein of the heated sample and the clottable protein of the non-heated sample.

(d) Determination of the water content on samples free of virus.

The determination of the water content was effected in the same manner as described in Example 1.

The virus titers measured after the heat treatment and the residual activity still present after the treatment can be taken from Table XII, which shows that the virus detection limit was reached after 5 h, the residual activity being satisfactory according to the methods listed.

EXAMPLE 11

(a) Production of an albumin-containing preparation.

To 10 l of human blood plasma 0.08 ethanol was added at a pH of 7.0 and a temperature of −20° C., a precipitate containing fibrinogen forming thereby. After separation of the precipitate, the ethanol concentration was increased to 0.25, and the temperature was lowered to −6° C. The precipitate forming, which contained immunoglobulin, was separated, and the ethanol concentration of the supernatant was increased to 0.40 at a pH of 6.5 and a temperature of −8° C., a further precipitation taking place. The precipitate was separated and discarded. For precipitating albumin, the pH of the supernatant was adjusted to 5.4 at the same temperature. The precipitate was separated by centrifuging and subjected to a further purification step, in that it was dissolved in water and the ethanol concentration was adjusted to 0.10 at a pH of 4.8 and a temperature of −2° C. The precipitated globulin was separated and discarded. The ethanol concentration of the supernatant was increased to 0.40, the temperature lowered to −8° C., and the pH adjusted to 5.1. The precipitate is albumin and was gathered by centrifuging and freeze-dried.

(b) Inactivation of a model virus.

An aqueous solution of the lyophilisate was adjusted to 50 mg of protein/ml and admixed with canine hepatitis virus in cell culture medium TCM 199 or with TCM 199 free of virus and freeze-dried. The freeze-dried albumin concentrate was adjusted to a water content of 0.07 and heated in closed containers—with and without virus—at 60° C. for various periods of time. Three samples each were drawn prior to heating and at certain times during the heating process for measuring the virus titer, on the one hand, and the molecular integrity and the water content, on the other hand.

The determination of the virus titer was effected in the same manner as in Example 5. The determination of the as in Example 5. The determination of the molecular integrity, namely the behaviour in the cellulose acetate electrophoresis and SDS-polyacrylamide gel electrophoresis, was effected in the same manner as described in Example 6.

(c) Determination of the water content on samples free of virus.

This determination was effected in the same manner as described in Example 1.

The virus titer measured after the heat treatment and the molecular integrity can be taken from Table XIII, which shows that the virus detection limit was reached already after one hour and the molecular integrity showed no change as compared to non-heated control samples.

EXAMPLE 12

Production of blood preparations by using a liquid medium in which they are insoluble.

A Factor VIII preparation produced as in Example 1(a) was adjusted to 50 mg of protein/ml, mixed with a Sindbis virus suspension in cell culture medium TCM 199 or with TCM 199 free of virus and freeze-dried. The freeze-dried Factor VIII preparation was adjusted to a water content of 0.09. Several containers with the freeze-dried Factor VIII samples—with and without virus—were each mixed with 10 ml of water-saturated chloroform (so as not to change the water content of the samples), closed, and heated for 10 h at 60° C. Three samples each were drawn prior to heating and at certain times during the heating process for measuring the virus titer, on the one hand, and the residual activity and the water content, on the other hand.

Before determining the virus titer and the residual activity, the samples were freed from the solvent by suction under vacuum.

The determination of the virus titer and the water content was effected as described in Example 1.

The virus titers measured after the heat treatment and the residual activity still present after the treatment can be taken from Table XIV, which shows there follows that the virus titer was below the detection limit after 3 h, while the residual activity amounted to 0.85.

In the same manner, the inactivation of canine hepatitis virus was tested in a FEIBA preparation and in a partial prothrombin complex preparation, the FEIBA preparation having been produced according to Example 5(a) and the partial prothrombin complex preparation according to Example 3(a). The determination of the virus titer was effected as described in Example 5. The virus titers measured after the heat treatment and the residual activity still present after the treatment can be taken from Table XIV.

In the following examples, the production of blood products is described, wherein the inactivation according to the invention is used for destroying any possibly present reproducible filterable pathogens.

EXAMPLE 13

Production of a Factor VIII preparation.

100 ml of fresh frozen plasma were thawed at a temperature of from 0° C. to +4° C. The cryoprecipitate formed was separated by centrifuging and dissolved in 10.5 l of a trisodium citrate solution that contained 50 mg of sodium pentosan sulphate/l and 30,000 units of aprotinin/l. The pH of the solution was adjusted to 6.3 and the temperature to +4° C. The precipitate formed was separated by centrifugation and discarded.

By adding ethanol up to a concentration of 0.08, the Factor VIII-containing fraction was precipitated. The precipitate formed was separated by centrifugation, dissolved in a glycin-citrate-NaCl buffer, freeze-dried, adjusted to a water content of 0.08 and heated for 10 h at 60° C. The determination of the Factor VIII activity after the heating process gave a residual activity of 0.92 (92%), as compared to a non-heated material.

For producing a galenic or pharmaceutical preparation, the inactivated powder was dissolved with distilled water under the addition of glycin-trisodium citrate-NaCl in a manner so as to obtain a solution containing 25 IU of Factor VIII per ml, 10 g of glycin/l, 10 g of trisodium citrate. $2H_2O/l$ and 5 g of sodium chloride/l. After adjusting the pH to 7.0, the solution was sterile-filtered, filled into the final containers with 20 ml per bottle, and freeze-dried. The determination of the Factor VIII activity of the freeze-dried material in the final containers gave 480 IU of Factor VIII/bottle.

EXAMPLE 14

Production of a Factor VIII-preparation after removal of neoproteins possibly formed during the inactivation.

46 l of fresh frozen plasma were thawed at a temperature of from 0° C. to +40° C. The cryoprecipitate formed was separated by centrifugation and dissolved in 960 ml of a trisodium citrate solution at 37° C. The pH of the solution was adjusted to 6.3, and the temperature to +4° C. The precipitate formed was separated by centrifugation and discarded. The Factor VIII-containing supernatant was freeze-dried, the lyophilisate adjusted to a water content of 0.075 (7.5%) and heat inactivated for 10 h at 60° C., so as to reliably destroy any reproducible filterable pathogens, such as hepatitis viruses that might be present. The determination of the Factor VIII activity after heating gave a residual activity of 0.95 (95%) of Factor VIII as compared to non-heated material.

Figure 4:
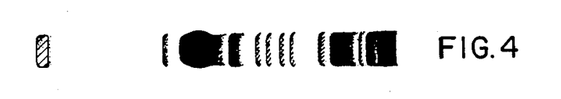
Figure 5:
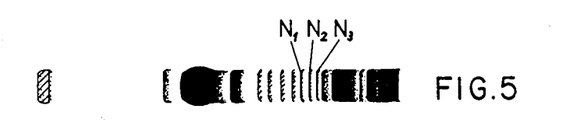

Samples of the non-heated and heated freeze-dried Factor VIII preparation were examined by means of SDS-polyacrylamide gel electrophoresis. With the non-heated sample, the band pattern denoted by FIG. 4 was obtained. With the heated sample, there resulted the band pattern denoted by FIG. 5, in which the bands denoted by $N_1$, $N_2$ and $N_3$ appeared, which are to be attributed to the occurrence of neoproteins during the thermal inactivation treatment. According to the invention, these neoproteins are to be removed by an after-treatment of the heated Factor VIII preparations. The after-treatment or further fractionation, respectively, was effected by dissolving the heated Factor VIII preparation in 900 ml of water and adding ethyl alcohol up to a concentration of 0.10. With this, a Factor VIII-containing fraction was precipitated, separated by centrifugation and dissolved in a glycin-citrate-NaCl buffer. The solution was converted into a galenic or pharmaceutical preparation, as described in Example 13.

Figure 6:
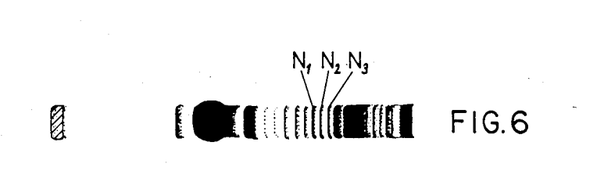
Figure 7:
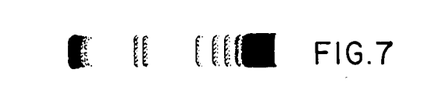

The SDS polyacrylamide gel electrophoresis of the purified fraction gave the band pattern denoted by FIG. 7, the examination of the supernatant of the 0.10 alcohol precipitation gave the band pattern denoted by FIG. 6. From this it becomes apparent that the neoproteins $N_1$, $N_2$ and $N_3$ remained in the supernatant of the alcohol precipitation, while the purified Factor VIII preparation did not contain these bands any more. With the alcohol fractionation described, other proteins are also removed. The Factor VIII activity in the fractionated preparation is substantially retained, i.e. to 0.70.

The thermal inactivation treatment according to the invention may be prolonged up to 100 h without losing the activities. The stability of important coagulation factors, when heating up to 100 h at certain temperatures and water contents within the scope of the present invention, can be taken from Table XV.

EXAMPLE 15

Production of a Factor VIII preparation by using a protective gas.

A Factor VIII-containing solution produced in the same manner as in Example 1 was mixed with a Sindbis virus suspension in cell culture medium TCM 199 or with TCM 199 free of virus and freeze-dried.

The freeze-dried Factor VIII concentrate was adjusted to a water content of 0.08 (8% by weight), brought into various "atmospheres" by 3 consecutive cycles of evacuation to 100 mbar and subsequent gas treatment with air, nitrogen, helium and argon, respectively, and heated for various periods of time in closed containers at a temperature of 80° C. From each variant, three samples each were drawn prior to heating and at certain times during the heating procedure for measuring the virus titer, on the one hand, and the residual activity of Factor VIII and the water content, on the other hand.

The determination of the virus titer, the residual activity of Factor VIII and the water content was effected as described in Example 1; the results can be taken from Table XVI. From this it becomes apparent that the residual activities or the yields of Factor VIII are considerably higher when heating in an inert gas atmosphere (nitrogen, helium, argon) than when heating in air. Yet the rate of the virus inactivation is independent of the atmosphere in which heating took place.

EXAMPLE 16

Production of a preparation containing partial prothrombin complex by using a protective gas.

A preparation produced in the same manner as in Example 3 which contained the coagulation Factors II, IX and X was mixed with a Sindbis virus suspension in cell culture medium TCM 199 or with TCM 199 free of virus and freeze-dried. The freeze-dried concentrate was adjusted to a water content of 0.08, brought into various "atmospheres" by 3 consecutive cycles of evacuation to 100 mbar and subsequent gas treatment with air, nitrogen, helium and argon, and heated for various periods in closed containers at a temperature of 90° C. From each variant, three samples each were taken before heating and at certain times during the heating procedure for measuring the virus titer, on the one hand, and residual activity of Factor IX and the water content, on the other hand.

The determination of the virus titer and the water content was effected as described in Example 1, the determination of the residual activity of Factor IX as described in Example 3.

The results can be taken from Table XVII. From this it becomes apparent that the residual activities or the yields of Factor IX are considerably higher when heating in an inert gas atmosphere (nitrogen, helium, argon) than when heating in air. Yet the rate of the virus inactivation is independent of the atmosphere in which heating took place.

TABLE I

| | | Factor VIII-preparation | | | | | | | | | | |
|---|---|---|---|---|---|---|---|---|---|---|---|---|
| water- | temperature | Sindbis virus titer ($\log_{10}$ TCID$_{50}$) after heating for | | | | | | | residual activity Factor VIII after heating for | | | |
| content | °C. | 0 | 0.1 | 0.3 | 1 | 3 | 10 | 30 h | 0.3 | 1 | 3 | 10 | 30 h |
| 0.50 | 60 | 5.1 | 2.6 | <1 | <1 | <1 | | | 0.80 | 0.59 | 0.38 | | |
| 0.30 | 60 | 5.2 | | 2.9 | <1 | <1 | | | 0.95 | 0.86 | 0.80 | | |
| 0.20 | 60 | 5.1 | | 3.4 | <1 | <1 | | | 1.00 | 0.95 | 0.92 | | |
| 0.08 | 60 | 5.0 | 4.7 | 3.6 | 2.0 | <1 | | | 1.00 | 1.00 | 1.00 | | |

TABLE I-continued

| | | Factor VIII-preparation | | | | | | | | | | | |
|---|---|---|---|---|---|---|---|---|---|---|---|---|---|
| water-content | temperature °C. | Sindbis virus titer ($log_{10}$ $TCID_{50}$) after heating for | | | | | | | residual activity Factor VIII after heating for | | | | |
| | | 0 | 0.1 | 0.3 | 1 | 3 | 10 | 30 h | 0.3 | 1 | 3 | 10 | 30 h |
| 0.08 | 80 | 4.9 | <1 | <1 | <1 | | | | 0.97 | 0.89 | | | |
| 0.015 | 60 | 3.7 | | | 3.7 | 2.7 | <1 | <1 | | | | 1.00 | 1.00 |
| 0.006 | 60 | 4.1 | | | 3.4 | 2.9 | 1.4 | <1 | | | | 1.00 | 1.00 |

TABLE II

| | | | Factor VIII-preparation | | | | | | | | |
|---|---|---|---|---|---|---|---|---|---|---|---|
| content of | | temperature | Sindbis virus titer ($log_{10}$ $TCID_{50}$) after heating for | | | | | residual activity Factor VIII after heating for | | | |
| methanol | water | °C. | 0 | 1 | 3 | 10 | 30 h | 1 | 3 | 10 | 30 h |
| 0.10 | 0.005 | 60 | 4.8 | 4.9 | 3.5 | <1.5 | <1.5 | 1.00 | 1.00 | 1.00 | 0.90 |
| | 0.005 | 60 | 5.1 | 5.3 | 4.6 | 3.6 | 2.1 | 1 | 1 | 1 | 1 |

TABLE III

| | | | Factor VIII-preparation | | | | | | | | |
|---|---|---|---|---|---|---|---|---|---|---|---|
| content of | | temperature | Sindbis virus titer ($log_{10}$ $TCID_{50}$) after heating for | | | | | residual activity Factor VIII after heating for | | | |
| mannitol | water | °C. | 0 | 1 | 3 | 10 | 30 h | 1 | 3 | 10 | 30 h |
| 0.10 | 0.002 | 60 | 6.6 | 5.6 | 5.0 | 4.0 | <1 | 1.00 | 1.00 | 1.00 | 1.00 |
| | 0.002 | 60 | 6.4 | 6.4 | 5.9 | 4.0 | 2.2 | 1.00 | 1.00 | 1.00 | 1.00 |

TABLE IV

| | | Preparation with partial prothrombin complex | | | | | | |
|---|---|---|---|---|---|---|---|---|
| water content | temperature °C. | bacteriophage T4-titer ($log_{10}$ PFU) after heating for | | | | residual activity Factor IX after heating for | | |
| | | 0 | 1 | 3 | 10 h | 1 | 3 | 10 h |
| 0.09 | 60 | 2.4 | 0 | 0 | 0 | 1.00 | 0.95 | 0.88 |
| 0.004 | 80 | 2.5 | 2.3 | 2.4 | 2.0 | | 1.00 | 1.00 |
| 0.004 | 90 | 2.6 | 2.7 | 2.7 | 2.0 | | 1.00 | 1.00 |

TABLE V

| | | Preparation with total prothrombin complex | | | | | | |
|---|---|---|---|---|---|---|---|---|
| water content | temperature °C. | Sindbis virus titer ($log_{10}$ $TCID_{50}$) after heating for | | | | | residual activity Factor IX after heating for | |
| | | 0 | 0.1 | 0.3 | 1 | 3 h | 1 | 3 h |
| 0.07 | 60 | 6.1 | 5.2 | 4.8 | 3.3 | <1 | 1.00 | 0.97 |

TABLE VI

| | | | FEIBA-preparation | | | | | | | | | | | | |
|---|---|---|---|---|---|---|---|---|---|---|---|---|---|---|---|
| content of | | temperature | Sindbis virus titer ($log_{10}$ $TCID_{50}$) after heating for | | | | | | | | residual activity FEIBA after heating for | | | | |
| water | ethanol | °C. | 0 | 0.05 | 0.1 | 0.2 | 0.3 | 1 | 3 | 10 | 30 h | 0.1 | 0.3 | 1 | 3 | 10 | 30 h |
| 0.007 | 0.10 | 60 | 3.9 | | | | | 3.5 | 2.8 | <1 | <1 | | | 1.0 | 1.0 | 1.0 | 0.90 |
| 0.07 | | 60 | 4.1 | | 3.8 | | 3.1 | 2.1 | <1 | | | | | 1.0 | 0.98 | | |
| 0.08 | | 90 | 4.7 | 2.9 | | <1 | <1 | <1 | <1 | | | 0.95 | 0.88 | | | | |
| 0.009 | | 60 | 5.2 | | | | | 4.8 | 4.8 | 4.6 | 1.7 | | | 1.0 | 1.0 | 1.0 | 1.0 |

TABLE VII

| | | FEIBA-preparation | | | | | | | | | | | |
|---|---|---|---|---|---|---|---|---|---|---|---|---|---|
| water content | temperature °C. | canine hepatitis virus titer ($log_{10}$ $TCID_{50}$) after heating for | | | | | | | residual activity FEIBA after heating for | | | | |
| | | 0 | 0.1 | 0.3 | 1 | 3 | 10 | 30 h | 1 | 3 | 10 | 30 h |
| 0.07 | 60 | 3.9 | 2.6 | 2.1 | <1 | <1 | | | 1.00 | 0.98 | | |
| 0.07 | 80 | 3.5 | <1 | <1 | <1 | <1 | | | 0.87 | 0.75 | | |
| 0.015 | 60 | 4.8 | | | 4.2 | 4.0 | 3.4 | 2.3 | | | 1.00 | 1.00 |

TABLE VIII

| | | Immunoglobulin-containing preparation | | | | | |
|---|---|---|---|---|---|---|---|
| water content | temperature °C. | Sindbis virus titer ($log_{10}$ $TCID_{50}$) after heating for | | | | | molecular integrity |
| | | 0 | 1 | 2 | 4 | 10 h | |
| 0.054 | 60 | 6.4 | 5.5 | 4.4 | 3.0 | <1 | no change as compared to non-heated control samples |

TABLE IX

| | | $C_1$-esterase inhibitor preparation | | | | | | | | |
|---|---|---|---|---|---|---|---|---|---|---|
| water content | temperature °C. | Sindbis virus titer ($log_{10}$ $TCID_{50}$) after heating for | | | | | residual activity (chromogenic substrate) after heating for | | | |
| | | 0 | 1 | 2 | 4 | 10 h | 1 | 2 | 4 | 10 h |
| 0.10 | 60 | 6.4 | 5.0 | 4.5 | 3.0 | <1 | 0.99 | 0.98 | 0.96 | 0.93 |

TABLE X

Plasminogen-containing preparation

| water content | temperature °C. | Sindbis virus titer ($\log_{10}$ TCID$_{50}$) after heating for 0 | 1 | 2 | 5 h | residual activity plasminogen after heating for 1 | 2 | 5 h |
|---|---|---|---|---|---|---|---|---|
| 0.058 | 60 | 5.6 | 4.5 | 3.7 | <1.5 | — | 0.94 | 1.02 |

TABLE XI

Plasma preparation

| water content | temperature °C. | Sindbis virus titer ($\log_{10}$ TCID$_{50}$) after heating for 0 | 0.3 | 1 h | residual activity aPTT after heating for 0.3 | 1 h |
|---|---|---|---|---|---|---|
| 0.052 | 60 | 5.4 | <1 | <1 | 0.97 | 0.91 |

TABLE XII

Fibrinogen and fibronectin-containing preparation

| water content | temperature °C. | Sindbis virus titer ($\log_{10}$ TCID$_{50}$) after heating for 0 | 1 | 2 | 5 h | | residual activity: thrombin time (c$_1$) clottable protein (c$_2$) after heating for 1 | 2 | 5 h |
|---|---|---|---|---|---|---|---|---|---|
| 0.063 | 60 | 4.9 | 2.9 | 1.5 | <1 | (c$_1$) | 0.80 | 0.80 | 0.70 |
|  |  |  |  |  |  | (c$_2$) | 0.91 | 0.85 | 0.73 |

TABLE XIII

Albumin-containing preparation

| water content | temperature °C. | canine hepatitis virus titer ($\log_{10}$ TCID$_{50}$) after heating for 0 | 1 | 2 | 4 h | molecular integrity |
|---|---|---|---|---|---|---|
| 0.07 | 60 | 3.2 | <1 | <1 | <1 | no change as compared to non-heated |

TABLE XIII-continued

Albumin-containing preparation

| water content | temperature °C. | canine hepatitis virus titer ($\log_{10}$ TCID$_{50}$) after heating for 0 | 1 | 2 | 4 h | molecular integrity |
|---|---|---|---|---|---|---|
|  |  |  |  |  |  | control samples |

TABLE XIV

Factor VIII-preparation

| water content | temperature °C. | Sindbis virus titer ($\log_{10}$ TCID$_{50}$) after heating for 0 | 0.3 | 1 | 3 h | residual activity of Factor VIII after heating for 3 h |
|---|---|---|---|---|---|---|
| 0.09 | 60 | 3.9 | 4.6 | 2.9 | <1 | 0.85 |

FEIBA-preparation

| water content | temperature °C. | canine hepatitis virus titer ($\log_{10}$ TCID$_{50}$) after heating for 0 | 0.1 | 0.3 | 1 | 3 h | residual activity of FEIBA after heating for 3 h |
|---|---|---|---|---|---|---|---|
| 0.08 | 60 | 2.9 | 2.0 | 2.0 | 2.1 | <1 | 0.83 |

Partial prothrombincomplex-preparation

| water content | temperature °C. | canine hepatitis virus titer ($\log_{10}$ TCID$_{50}$) after heating for 0 | 0.1 | 0.3 | 1 | 3 h | residual activity of Factor IX after heating for 3 h |
|---|---|---|---|---|---|---|---|
| 0.08 | 60 | 2.6 | 1.8 | <1 | <1 | <1 | 0.87 |

TABLE XV

Stability of the coagulation factors

| product | water content | temperature °C. | residual activity after heating for 10 | 30 | 100 h | |
|---|---|---|---|---|---|---|
| Factor VIII-concentrate | 0.08 | 60 | 0.94 | 0.85 | 0.47 | Factor VIII |
| FEIBA | 0.07 | 60 | 0.95 | 0.82 | 0.67 | FEIBA |
| Total prothrombin-complex | 0.07 | 60 | 0.91 | 0.79 | 0.38 | Factor IX |
| Partial prothrombin complex | 0.09 | 60 | 0.88 | 0.73 | 0.33 | Factor IX |

TABLE XVI

Factor VIII-preparation

| water content | temperature °C. | atmosphere | Sindbis virus titer (log TCID$_{50}$) after heating for 0 | 0.3 | 1 | 3 | 10 h | residual activity of Factor VIII after heating for 1 | 3 | 10 h |
|---|---|---|---|---|---|---|---|---|---|---|
| 0.08 | 80 | air | 4.8 | <1 | <1 | <1 | <1 | 0.85 | 0.53 | 0.28 |
| 0.08 | 80 | nitrogen | 5.0 | <1 | <1 | <1 | <1 | 0.95 | 0.83 | 0.60 |
| 0.08 | 80 | helium | 4.7 | <1 | <1 | <1 | <1 | 0.97 | 0.85 | 0.62 |
| 0.08 | 80 | argon | 4.9 | <1 | <1 | <1 | <1 | 0.98 | 0.85 | 0.62 |

TABLE XVII

Preparation with partial prothrombin complex

| water content | temperature °C. | atmosphere | Sindbis virus titer (TCID$_{50}$) after heating for 0 | 0.3 | 1 | 3 | 10 h | residual activity of Factor IX after heating for 1 | 3 | 10 h |
|---|---|---|---|---|---|---|---|---|---|---|
| 0.08 | 90 | air | 4.7 | <1 | <1 | <1 | <1 | 0.63 | 0.30 | 0.07 |
| 0.08 | 90 | nitrogen | 4.9 | <1 | <1 | <1 | <1 | 0.82 | 0.55 | 0.22 |
| 0.08 | 90 | helium | 5.1 | <1 | <1 | <1 | <1 | 0.75 | 0.47 | 0.14 |
| 0.08 | 90 | argon | 4.8 | <1 | <1 | <1 | <1 | 0.70 | 0.42 | 0.12 |

What we claim is:

1. A method of inactivating viable filterable pathogens in a blood product, which comprises: placing said blood product in a solid state in a closeable treating zone in the presence of a hydroxyl group-containing compound selected from the group consisting of water, methanol, ethanol, and mixtures thereof, and closing said treating zone; maintaining the content of said hydroxyl group-containing compound in said treating zone to provide said blood product with a content of hydroxyl group-containing compounds of more than 0.05 (5% by weight) and less than 0.70 (70% by weight); and heating said blood product in the solid state in the closed treating zone at a temperature of between 50° and 121° C. to increase the partial vapor pressure of said hydroxyl group-containing compound, to thereby inactivate viable filterable pathogens.

2. A method as set forth in claim 1, wherein the content of said hydroxyl group-containing compound is maintained to provide said blood product with a content of hydroxyl group-containing compound of more than 0.05 (5% by weight) and less than 0.40 (40% by weight).

3. A method as set forth in claim 2, wherein said hydroxyl group-containing compound is water, said water being present in the blood product at between about 0.06 (6% by weight) and about 0.30 (30% by weight), and said heating being at a temperature of from 50° to 90° C.

4. A method as set forth in claim 1, wherein said blood product is heated in the presence of an inert gas free of oxygen.

5. A method as set forth in claim 4, wherein said blood product is heated in the presence of an oxygen-binding substance.

6. A method as set forth in claim 4, wherein said inert protective gas is nitrogen.

7. A method as set forth in claim 1, wherein the content of said hydroxyl group-containing compound is maintained by the addition of a hydroxyl group-containing compound in gaseous form.

8. A method as set forth in claim 7, wherein said content of said hydroxyl group-containing compound is less than 0.40 (40% by weight).

9. A method as set forth in claim 7, wherein said hydroxyl group-containing compound is water vapor.

10. A method as set forth in claim 9, wherein the partial vapor pressure of said hydroxyl group-containing compound is increased to between about 0.1 and about 2 bars.

11. A method as set forth in claim 1, wherein said viable filterable pathogens are hepatitis viruses.

12. A method as set forth in claim 1, wherein said viable filterable pathogens are agents capable of transmitting AIDS (acquired immune deficiency syndrome).

13. A method as set forth in claim 1, wherein said blood product is heated for a period of from 1 s to 100 h.

14. A method of producing blood products selected from the group consisting of enzymes, proenzymes, enzyme inhibitors, immunoglobulins, albumin, plasminogen, fibrinogen, fibronectin and plasma and mixtures thereof by using a method as set forth in claim 1, wherein said inactivation is effected at any desired stage of said product method.

15. A method as set forth in claim 14, further comprising converting said blood products into a galenic or pharmaceutical preparation after said inactivation.

16. A method as set forth in claim 1, further comprising additional fractionation steps for liberating said heat-inactivated blood products from any neoproteins or neoantigens formed during heat-inactivation.

17. A blood product, selected from the group consisting of enzymes, proenzymes, enzyme inhibitors, immunoglobulins, albumin, plasminogen, fibrinogen, fibronectin and plasma, produced by fractionation, wherein the blood product has been treated, at any desired stage of the fractionation, by a method which comprises: placing said blood product in a solid state in a closeable treating zone in the presence of a hydroxyl group-containing compound selected from the group consisting of water, methanol, ethanol, and mixtures thereof, and closing said treating zone; maintaining the content of said hydroxyl group-containing compound in said treating zone to provide said blood product with a content of hydroxyl group-containing compound of more than 0.05 (5% by weight) and less than 0.70 (70% by weight); and heating said blood product in the solid state in the closed treating zone at a temperature of between 50° and 121° C. to increase the partial vapor pressure of said hydroxyl group-containing compound, to thereby inactivate viable filterable pathogens.

18. A composition comprising the blood product of claim 17 in a pharmaceutically acceptable carrier.

19. A blood product, selected from the group consisting of enzymes, proenzymes, enzyme inhibitors, immunoglobulins, albumin, plasminogen, fibrinogen, fibronectin and plasma, produced by fractionation, wherein the blood product has been treated, at any desired stage of the fractionation, by a method which comprises: placing said blood product in a solid state in a closeable treating zone in the presence of a hydroxyl group-containing compound selected from the group consisting of water, methanol, ethanol, and mixtures thereof, and closing said treating zone; maintaining the content of said hydroxyl group-containing compound in said treating zone to provide said blood product with a content of hydroxyl group-containing compound of more than 0.05 (5% by weight) and less than 0.40 (40% by weight); and heating said blood product in the solid state in the closed treating zone at a temperature of between 50° and 121° C. to increase the partial vapor pressure of said hydroxyl group-containing compound, to thereby inactivate viable filterable pathogens.

20. A composition comprising the blood product of claim 19 in a pharmaceutically acceptable carrier.

* * * * *

UNITED STATES PATENT AND TRADEMARK OFFICE
CERTIFICATE OF CORRECTION

PATENT NO. : 4,640,834

DATED : Feb. 3, 1987

INVENTOR(S) : Johann Eibl et al.

It is certified that error appears in the above-identified patent and that said Letters Patent is hereby corrected as shown below:

Column 2, line 39, "method" should read -- methods --;

Column 3, line 22, "10 h:" should read -- 10 h. --; and

Column 4, line 29, "heat-activated" should read -- heat-inactivated --.

Signed and Sealed this

First Day of October, 1991

Attest:

HARRY F. MANBECK, JR.

Attesting Officer

Commissioner of Patents and Trademarks